United States Patent [19]
Polaschegg

[11] Patent Number: 4,966,579
[45] Date of Patent: Oct. 30, 1990

[54] APPARATUS FOR DOSED CONTINUOUS SIMULTANEOUS INFUSION OF A PLURALITY OF INFUSION SOLUTIONS OR MEDICAMENTS

[75] Inventor: Hans-Dietrich Polaschegg, Oberursel, Fed. Rep. of Germany

[73] Assignee: Fresenius AG, Bad Homburg, Fed. Rep. of Germany

[21] Appl. No.: 355,151

[22] Filed: May 22, 1989

[30] Foreign Application Priority Data

May 21, 1988 [DE] Fed. Rep. of Germany ....... 3817411

[51] Int. Cl.$^5$ .............................................. A61M 31/00
[52] U.S. Cl. ........................................ 604/65; 604/131
[58] Field of Search ..................... 604/131, 65, 66, 67, 604/191, 410, 132, 154

[56] References Cited

U.S. PATENT DOCUMENTS

| | | | |
|---|---|---|---|
| 4,710,166 | 12/1987 | Thompson et al. | 604/65 |
| 4,743,228 | 5/1988 | Butterfield | 604/65 |
| 4,828,545 | 5/1989 | Epstein et al. | 604/66 |
| 4,838,856 | 6/1989 | Mulreany et al. | 604/67 |

Primary Examiner—John D. Yasko
Attorney, Agent, or Firm—Poms, Smith, Lande & Rose

[57] ABSTRACT

An apparatus is described for dosed continuous simultaneous infusion of several solutions or medicaments which are arranged in a plurality of containers (25, 26) or syringes (3, 4). From said containers (25, 26) or syringes (3, 4) connecting conduits or tubes (18-21) lead which are connected via a junction piece (27) to a patient conduit (23). In each of the connecting conduits (18-21) a pump (1-4) and a clamp (5-8) are provided which are each controlled via a central processing unit (17). Downstream of said actuating means in the patient conduit (23) a flow element (14) is provided which on detection of a flow stop causes the control means (17) to deactivate the entire apparatus.

9 Claims, 1 Drawing Sheet

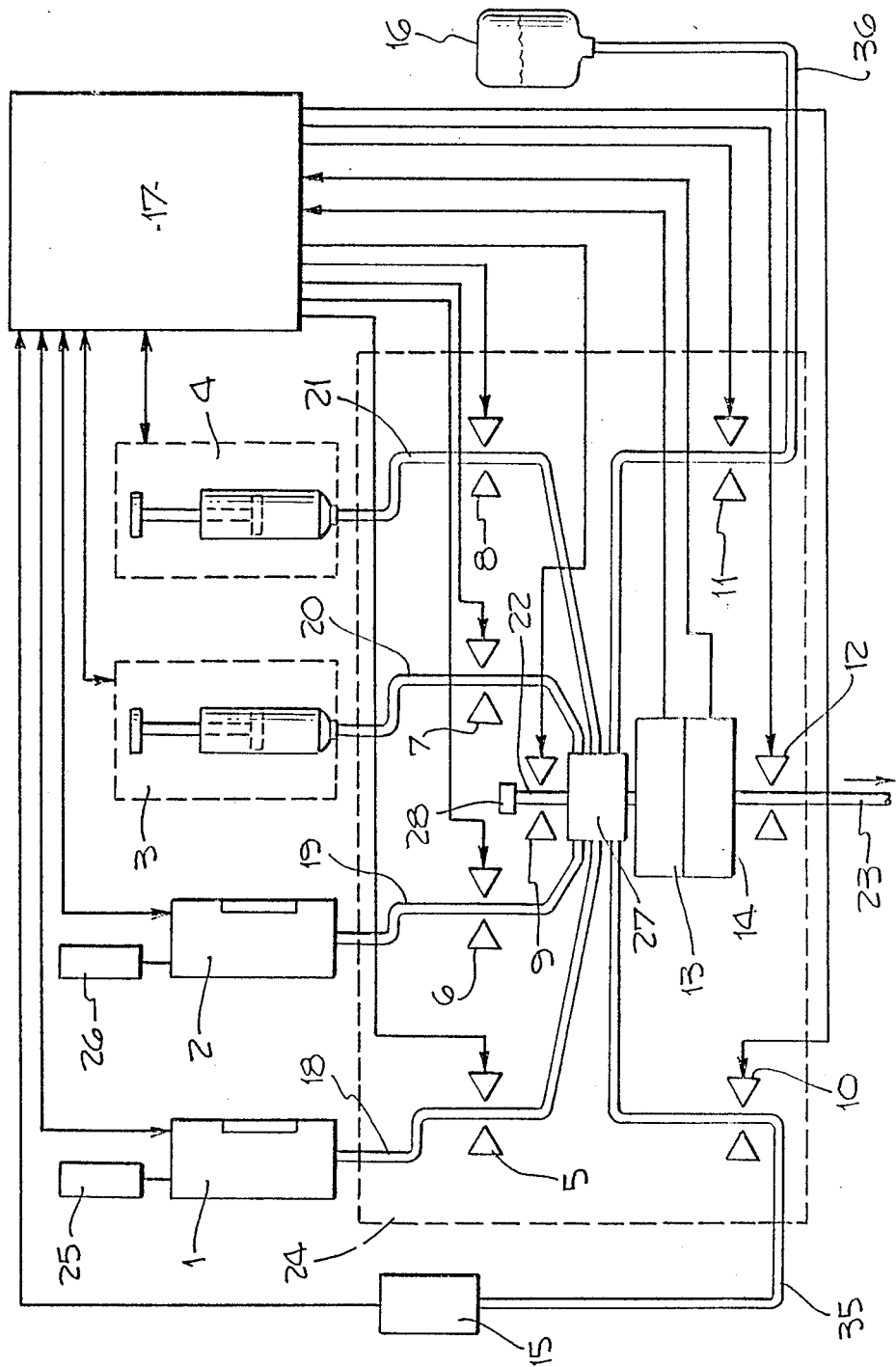

APPARATUS FOR DOSED CONTINUOUS SIMULTANEOUS INFUSION OF A PLURALITY OF INFUSION SOLUTIONS OR MEDICAMENTS

The invention relates to an apparatus for dosed continuous simultaneous infusion of a plurality of infusion solutions or medicaments comprising at least one pump, delivery conduits which lead from the containers containing the infusion or medicament solutions and are connected via a junction piece to a common patient conduit, valves which are provided in each delivery conduit, a flow element detecting the flow and a control unit which is connected as regards signals to the valves, the pump and the flow element.

Modern intensive care uses to an ever increasing extent infusion pumps for artificial parenteral feeding, for continuous and exactly dosed administration of medicaments and more recently also for controlled supply of highly active medicaments in dependence upon physiological parameters.

As a rule, three to four different medicaments or infusion solutions are administered with the aid of a plurality of pumps or control means independent of each other via an access to the blood circulation of the patient which consists generally of a central venous catheter. In exceptional cases up to twelve pumps can be connected to a patient access.

Generally, for this purpose pumps are used with the associated disposable tube articles which are connected downstream of the pump via three-way cocks to a collective conduit which leads to the catheter. Socalled gravity infusion devices and means for measuring the central venous pressure are usually additionally connected to the same patient conduit likewise via three-way cocks.

Such arrangements have the following disadvantages:

1. The individual construction is as a rule so complicated that there is a danger of confusion.
2. The individual plugging together of infusion conduits, three-way cocks and the like involves a risk of contamination.
3. In a combination of pumps and gravity infusion devices on placing the patient access conveying of infusion solution from the pumps to the gravity infusion system takes place because the pressure detection systems of the pumps, if indeed they are provided at all, do not respond to a pressure of at the most 0.2 bar caused by gravity. The infusion stop is thus not detected and remains unrecognized until detected indirectly with the aid of patient monitoring.
4. If the infusion conduit is interrupted downstream of the pump (e.g. by a mistakenly closed three-way cock) the pump or pumps continue to operate until due to an excessive pressure in the conduit the pressure detecting system of a pump responds or the pump ceases to deliver.

Due to the deformability of the infusion conduits a storage volume is formed which on opening of the three-way cock or after eliminating the interruption can suddenly discharge into the patient.

The mistaken closure of a three-way cock occurs relatively frequently because for example for taking specimens and also for measuring the central venous pressure (CVP measurement) the connecting cocks to the pumps must be momentarily closed.

Admittedly, there are certain behaviour rules and regulations to be followed to avoid the aforementioned risks but these require great power of concentration of the user and involve increased costs. For example, it is considered inexpert to combine a pump infusion with a gravity infusion. This leads to an infusion pump having to be used even in cases where this is not justified by the accuracy requirement of the delivery of the medicament or infusion solution and this leads to increased costs.

To avoid some of the disadvantages mentioned socalled multiple infusion systems have been developed. DE-PS No. 3,329,977 discloses an apparatus for dosed infusion of solutions from several infusion containers. A plurality of gravity infusion means having drip counters are connected via exit lines into which clamping valves are incorporated to a collective conduit which leads to the patient. Downstream in said patient conduit firstly a flow sensor is connected and thereafter a delivery pump. All the valves and the flow sensor as well as the pump are connected to a control unit.

The infusion rate to be chosen by the physician for the individual solutions is converted in the control device to proportional drip numbers. Each valve remains open until the drip number associated with said passage is achieved. Thereafter the valve is closed and the valve of the next passage opened. In each case specific drip numbers are determined and supplied to the collective conduit until a switchover takes place. This apparatus has a number of disadvantages. The infusion takes place sequentially, i.e. the delivery of the individual solutions does not take place continuously. Moreover, the delivery of a highly effective medicament at lower rate and at the same time for example a parenteral nutritional solution at high rate is not possible. A further disadvantage resides in that the single pump operates with constant delivery rate and a defect in the pump leads to an uncontrolled infusion.

The problem underlying the invention is to avoid the aforementioned disadvantages and provide an apparatus for dosed infusion which permits the simultaneous delivery of highly effective medicaments with small infusion rates with high accuracy, with high infusion rates with average accuracy and high infusion rates with moderate accuracy and compared with conventional apparatus not only a simpler and more secure use is achieved but also a saving in costs.

This problem is solved by an apparatus according to the characterizing features of claim 1.

In the multiple infusion apparatus according to the invention a plurality of pumps and gravity means can be combined with each other. Thus, syringe infusion pumps, which ensure high accuracy at low infusion rates, can be combined with linear peristaltic infusion pumps, which ensure an average accuracy at high infusion rates. For high infusion rates with moderate accuracy gravity infusion means are provided. Both the pumps and the gravity infusion means are connected downstream to delivery conduits which open into a common patient conduit. In each of said delivery conduits clamping valves are incorporated which are connected to a central processing unit which also comprises a control unit. The central processing or computing unit is connected at the same time to the pumps so that the predetermined infusion rates which have been entered into the central processing unit can be passed on to the pumps. The central processing unit can further be equipped with a bar code reader which makes it possible to acquire the data of infusion containers themselves marked with a bar code. The central processing unit then has both information on the composition of the connected infusion solution and on the rate with which it is to be administered. Consequently, the central processing unit can calculate both the total amount of the liquid amounts administered at any instant to the patient as well as the amount of energy and specific substance amount (sodium, potassium, other electrolyte, amino acids, fats, glucose, and the like) and display this information on a screen or output said information on a printer. Instead of a bar code reader other reading means may be used which permit automatic acquistion. If such means are not provided on the infusion solution container manual entry is possible. A valve is also arranged in the patient conduit.

It is important in the apparatus according to the invention for the flow element to be arranged downstream of the pumps and the control unit to deactivate the apparatus on detection of a fluid stop by the flow element by closing the valves and switching off the pump.

Preferably, the flow element, is arranged in the patient conduit.

The flow element in the common patient conduit downstream of the pumps or downstream of the unification of all the infusion conduits serves to detect the interruption of the infusion, for example by a blockage of the catheter. A blockage of the catheter, whether by ending of the supply conduit or for other reasons, can have significant and grave consequences for the patient. Firstly, the patient is not supplied with the medicaments present in the infusion solutions. Since these may include medicaments having half-life times of a few minutes (for example sodium nitroprusside used for regulating blood pressure), even after a short time this can lead to a dangerous rise of the blood pressure of the patient. However, the pumping effect can also lead to a rise of the pressure in the infusion conduits in front of the blockage point. Since said conduits or tubes are elastic a certain amount of infusion solution is stored. If the result is finally an infusion stop because a pressure detector usually present in infusion pumps detects this pressure increase and the stoppage point is thereafter eliminated, the stored volume is suddenly infused into the patient and this gives rise to excessive infusion.

The flow element downstream of the pump can detect an interruption of the flow before the pressure has built up. Although there is still a tubing section of certain elasticity downstream of the flow element, the volume storable therein is substantially less than in the overall system. In addition, in the event of blockage and pressure buildup a substantially greater part of the flow delivered by the pumps is stored in the larger volume of the tubing system above, i.e. upstream, of the flow element and the flow through the flow element into the tubing piece disposed downstream of said flow element is thereby greatly reduced. Although at this instant the flow does not drop to zero it will decrease by a great amount, that is more than 50%. This change can easily be detected. As a result of such a detection not only the valves are stopped but also the pumps. The pumps should under no circumstances work against the valves, except for test or control purposes, since otherwise a storage volume will be built up in front of the valves.

Preferably, the flow element consists of a drip detector. In addition, a CVP measuring means may also be connected to said patient conduit.

According to a further embodiment in the patient conduit an air detector may additionally be arranged which is likewise connected to the central processing unit.

Advantageously, said tubing clamping valves are mechanically actuated and electrically monitored or electrically actuated by the central processing unit and redundantly monitored.

Preferably, the clamping valves and the sensors are combined in a socalled sensor and valve block.

If at least one gravity infusion means is connected the flow element may also be arranged in the corresponding connecting conduit to the gravity infusion means instead of in the patient conduit. Since the gravity infusion means usually have a drop regulator with manual or automatically operating clamp said regulator can take on the function of the flow element. The signal from the associated drop senor is employed to detect a blockage of the patient conduit.

The detection is possible as follows:

In a normal case the pumps and parallel thereto the gravity infusion means deliver infusion solution to the patient. If the patient conduit is interrupted for example by a blockage of the catheter due to the pumping action the pressure in the system is increased and as a result the drip rate in the gravity operated system drops and finally becomes zero: The pumps deliver backwards into the gravity infusion system. This is in itself a dangerous state because it means that the interruption of the infusion is not detected. However, in the construction according to the invention this state is detected by the drip sensor and consequently the apparatus can be deactivated.

The apparatus according to the invention permits non-risk combination of the pumps with connected gravity infusion means because an interruption of the flow to the patient is detected by the flow element. The valves electrically controlled or monitored by the central processing unit prevent a valve remaining unintentionally closed although the pumps have been started. If a CVP measuring means is connected to the patient conduit an automatic execution of this measurement is additionally possible. The central venous pressure can be detected with the aid of a manual or automatically closable water column. A device for automatic detection of the water column may advantageously be constructed as ultrasonic level sensor, an ultrasonic reflecting point being provided in the rise pipe as reference distance.

The air detector may be a known ultrasonic air detector. Said air detector is advantageously connected to the valve in the patient conduit so that the latter is closed when the air sensor responds.

To vent the conduits a vent means is advantageously connected to the patient conduit. Firstly, all the valves in the delivery conduits are closed, this being done by the central processing and control unit. If the patient conduit is equipped with a combination of hydrophobic filter and check valve the vent valve of the vent means can also remain closed. Otherwise, said valve is opened by the control unit.

Thereafter the valve in the first delivery conduit is opened and the pump disposed in said branch set in operation, delivering at high rate until the air sensor reports freedom from air. Said valve in the delivery conduit and the vent valve are then closed and the pump stopped.

Thereafter, the valve in the patient conduit and the valve in the second delivery conduit are opened and the pump in said branch set in operation. Said pump first delivers air with which the residue of solution remaining in the patient conduit from the previous filling operation is pumped out of said conduit and discarded. In this manner a flushing of the tubing is simultaneously effected. As soon as the air sensor responds the valve in the patient conduit is closed and the vent valve opened. The delivery of the pump is continued until the air sensor reports freedom from air. The pump is stopped and the valve in said delivery conduit again closed. In this manner the other delivery conduits are also vented.

On completion of this step the patient conduit is connected to the patient and the infusion can start.

If in accordance with a further embodiment a CVP measuring means is connected to the patient conduit said means is set in operation in that the valve in the supply line to the patient conduit and the valve in a delivery line are opened and all the other valves remain closed. The pump connected to said delivery conduit is set in operation and delivers solution until the CVP measuring means is vented or responds. The gravity infusion means is set in operation in analogous manner. For this purpose the valve in the delivery conduit of the gravity infusion means and the vent valve are opened. Under the action of gravity infusion solution enters the delivery conduit and expels the air therefrom. As soon as the air sensor has reported freedom from air said valves, i.e. the valve in the delivery conduit to the infusion means and the vent valve, are closed again.

If a gravity infusion means with a drop sensor is connected to the delivery conduit and said drop sensor is connected as regards signals to the central processing and control unit then in known manner the latter can open and close the valve in the delivery conduit so that on an average a predetermined drip rate is achieved. This means that the system operates as drip infusion regulator.

Hereinafter an exemplary embodiment will be explained in detail with the aid of the drawing.

The FIGURE shows a multiple infusion means which comprises two linear peristaltic infusion pumps 1 and 2, two syringe infusion pumps 3 and 4, a gravity infusion means 16 and a CVP measuring means 15. The linear peristaltic infusion pumps 1 and 2 are connected respectively to infusion solution containers 25 and 26. Each infusion pump, like the gravity infusion means, is connected to a delivery conduit which are designated by 18, 19, 20, 21 and 36. In each delivery conduit there is a clamping valve 5, 6, 7, 8, 11 which are connected as regards signals to a central processing and control unit 17. Said central processing and control unit is connected at the same time to the infusion pumps 1, 2, 3 and 4. The delivery rate of said infusion pumps is controlled by the central processing and control unit in accordance with a predetermined program.

The delivery conduits 18, 19, 20, 21 and 36 and the supply line 35, controlled by clamping valve 10, to the CVP measuring means 15 are connected via a junction piece 27 jointly to the patient conduit 23. In said patient conduit or tube 23 an air conduit 23. In said patient conduit or tube 23 an air sensor 13, a flow element 14 and a further valve 12 are arranged. The air sensor, the flow sensor and said valve 12 are likewise connected to the central processing control unit 17.

Additionally connected to the junction piece 27 is a vent means 22 in the form of a connecting tube piece with the valve 9 which is likewise connected to the central processing and control unit 17. Instead of the valve 9, a hydrophobic filter 28 possibly having a check valve, not shown, can close the vent means 22 in sterile manner with respect to the surroundings. The various parts may be housed in housing 24, as indicated.

Said multiple infusion means thus consists of various infusion means with which different amounts of infusion solutions or medicaments can be administered with different accuracies. By arranging the air sensor 13 and flow sensor 14 in the patient conduit the pressure and air sensors usually disposed in the delivery conduits can be dispensed with. This arrangement according to the invention ensures a high degree of safety for the patient because an interruption of the flow to the patient is detected by the flow sensor 14 and via the central processing and control unit the corresponding valves in the delivery conduits or the safety valve 12 can then immediately be closed. Moreover, the multiple infusion apparatus affords the possibility of connecting a CVP measuring means 15 to the patient conduit 23 as well.

I claim:

1. Apparatus for dosed continuous simultaneous infusion of a plurality of infusion or medicaments solutions comprising at least one pump, delivery conduits which lead from containers containing the infusion or medicaments solutions and are connected via a junction piece to a common patient conduit, valve which are provided in each delivery conduit, a flow sensor detecting the flow in the patient conduit and a control unit which is operatively connected to the valves, the pump and the flow sensor, characterized in that the flow sensor (14) is arranged downstream of the pump (1-4) and that the control unit (17) causes the valves (5-8) to close on detection of a fluid stop by the flow sensor.

2. Apparatus according to claim 1, characterized in that the flow sensor (14) is a drip detector.

3. Apparatus according to claim 1 or 2, characterized in that a vent means (22) is connected to the junction piece (27).

4. Apparatus according to claim 3, characterized in that the vent means (22) is formed as tube piece on which a valve (9) engages.

5. Apparatus according to claim 3, characterized in that the vent means (22) is closed with a hydrophobic sterile filter (28).

6. Apparatus according to any one of claims 1 to 5, characterized in that in the patient conduit (23) upstream of the flow sensor (14) an air detector (13) is arranged which is connected to the control unit (17) which in response to the signal of the air detector (13) in the vent phase controls the valves (5, 8, 9, 11) and the pump (1-4) in accordance with a predetermined program.

7. Apparatus according to any one of claims 1 to 6 characterized in that downstream of the flow sensor (14) in the patient conduit (23) a further shutoff valve (12) is arranged which on detection of a fluid stop by the flow sensor (14) closes the patient conduit (23) with the aid of the control unit (17).

8. Apparatus according to any one of claims 1 to 7 characterized in that to the junction piece (27) a gravity infusion means (16) is connected via a connecting conduit (36) into which a valve (11) is inserted.

9. Apparatus according to any one of claims 1 to 8, characterized in that to the junction piece (27) a CVD measuring means (15) is connected via a further connecting conduit (35) which can be shut off by a valve (10).

* * * * *